US006572840B1

(12) United States Patent
Toler

(10) Patent No.: US 6,572,840 B1
(45) Date of Patent: Jun. 3, 2003

(54) STABLE MICROBUBBLES COMPRISED OF A PERFLUOROPROPANE ENCAPSULATED LIPID MOIETY FOR USE AS AN ULTRASOUND CONTRAST AGENT

(75) Inventor: Maria R. Toler, Chelmsford, MA (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 09/621,569

(22) Filed: Jul. 21, 2000

Related U.S. Application Data

(60) Provisional application No. 60/146,059, filed on Jul. 28, 1999.

(51) Int. Cl.[7] .................................................. A61B 8/00
(52) U.S. Cl. ...................................... 424/9.52; 424/9.51
(58) Field of Search ............................. 424/9.52, 9.51, 424/450; 516/11, 77

(56) References Cited

U.S. PATENT DOCUMENTS

| 4,466,442 A | 8/1984 | Hilmann et al. |
| 5,088,499 A | 2/1992 | Unger |
| 5,228,446 A | 7/1993 | Unger et al. |
| 5,547,656 A | 8/1996 | Unger et al. |
| 5,585,112 A | 12/1996 | Unger et al. |
| 5,705,187 A | 1/1998 | Unger |
| 5,715,824 A | 2/1998 | Unger et al. |
| 5,769,080 A | 6/1998 | Unger et al. |
| 5,773,024 A | 6/1998 | Unger et al. |
| 6,146,657 A | * 11/2000 | Unger et al. ................. 424/450 |

FOREIGN PATENT DOCUMENTS

| WO | 9217212 | 10/1992 |
| WO | 9221382 | 10/1992 |
| WO | 96/08234 | 3/1996 |
| WO | 97/40679 | 11/1997 |
| WO | 98/10798 | 3/1998 |
| WO | 99/30620 | 6/1999 |
| WO | 99/49899 | 10/1999 |

OTHER PUBLICATIONS

Sharma et al., Drug Development and Industrial Pharmacy, US New York, 1998, 14, No. 15/17, 2371–2376.

* cited by examiner

Primary Examiner—Michael G. Hartley
(74) Attorney, Agent, or Firm—Paul D. Golian

(57) ABSTRACT

Novel contrast agents for ultrasound diagnosis and a reproducible process for making the same are described, wherein the contrast agents comprise a microbubble composition comprising a lipid shell, a stabilizer coated on the lipid shell and perfluoropropane gas encapsulated in the lipid shell.

42 Claims, 2 Drawing Sheets

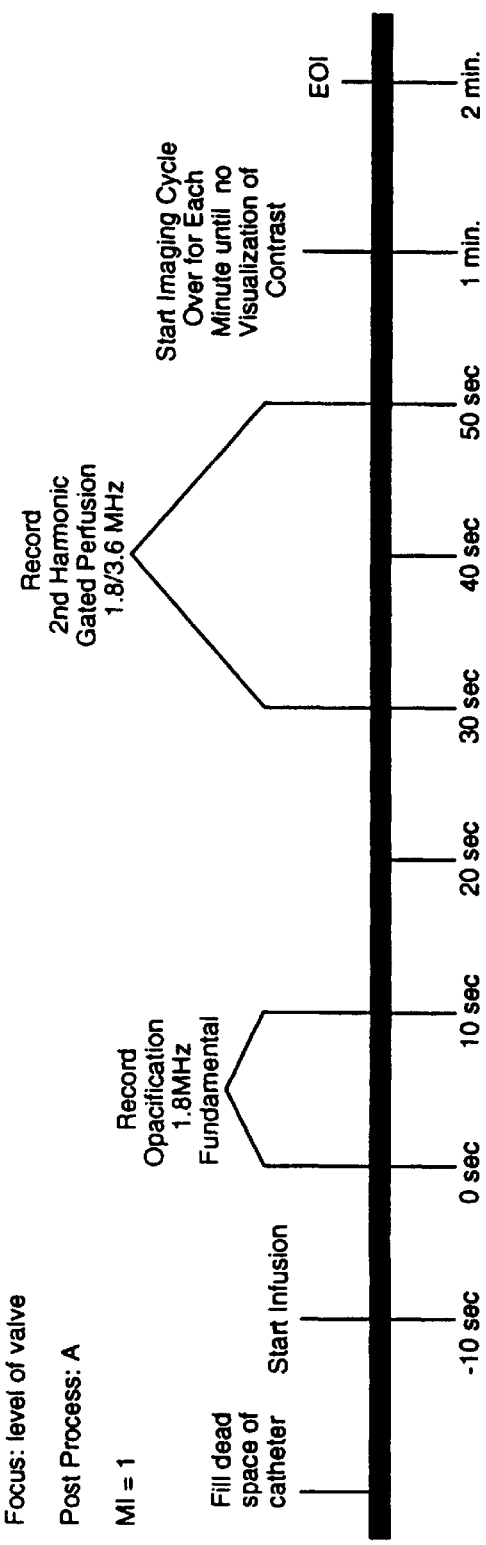

STABLE MICROBUBBLES COMPRISED OF A PERFLUOROPROPANE ENCAPSULATED LIPID MOIETY FOR USE AS AN ULTRASOUND CONTRAST AGENT

This application claims the benefit of U.S. Provisional Application No.60/146059, filed Jul. 28, 1999.

FIELD OF THE INVENTION

This invention relates generally to contrast agents for ultrasound diagnosis and a process for making the same. In particular, the present invention relates to a microbubble composition comprising a lipid shell, a stabilizer coated on the lipid shell and perfluoropropane gas encapsulated in the lipid shell. The lipid shell comprises 1,2-dipalmitoyl-sn-glycero-3-phosphatidic acid, monosodium salt, 1,2-dipalmitoyl-sn-glycero-3-phosphatidylcholine and 1,2 dipalmitoyl-sn-glycero-3-phosphatidylethanolamine, monosodium salt and the stabilizer comprises a high molecular weight polymer. In the microbubble composition of the invention, the lipid component is not conjugated to the stabilizer.

BACKGROUND OF THE INVENTION

Ultrasound is a valuable diagnostic imaging technique for studying various areas of the body, for example, the vasculature, including tissue microvasculature. Ultrasound provides certain advantages over other diagnostic techniques. For example, diagnostic techniques involving nuclear medicine and X-rays generally results in exposure of the patient to ionizing electron radiation. Such radiation can cause damage to subcellular material, including deoxyribonucleic acid (DNA), ribonucleic acid (RNA) and proteins. Ultrasound does not involve such potentially damaging radiation. In addition, ultrasound is relatively inexpensive relative to other diagnostic techniques, including computed tomography (CT) and magnetic resonance imaging (MRI), which require elaborate and expensive equipment.

Ultrasound involves the exposure of a patient to sound waves. Generally, the sound waves dissipate due to absorption by body tissue, penetrate through the tissue or reflect off of the tissue. The reflection of sound waves off of tissue, generally referred to as backscatter or reflectivity, forms the basis for developing an ultrasound image. In this connection, sound waves reflect differentially from different body tissues. This differential reflection is due to various factors, including the constituents and the density of the particular tissue being observed. Ultrasound involves the detection of the differentially reflected waves, generally with a transducer that can detect sound waves having a frequency of one megahertz (Mhz) to ten Mhz. The detected waves can be integrated into an image which is quantitated and the quantitated waves converted into an image of the tissue being studied.

Ultrasound imaging techniques generally also involve the use of contrast agents. Contrast agents are used to improve the quality and usefulness of images which are obtained via ultrasound. Exemplary contrast agents include, for example, suspensions of solid particles, emulsified liquid droplets, and gas-filled bubbles. See, e.g., Hilmann et al., U.S. Pat. No. 4,466,442; Unger, U.S. Pat. No. 5,088,499; Unger, U.S. Pat. No. 5,547,656; Unger and Wu, U.S. Pat. No. 5,228,446; Unger et al., U.S. Pat. No. 5,715,824; Unger and Wu, U.S. Pat. No. 5,769,080; Unger, U.S. Pat. No. 5,705,187; Unger et al., U.S. Pat. No. 5,773,024; Unger et al., U.S. Pat. No. 5,535,112; and published International Patent Applications WO 92/17212 and WO 92/21382.

The quality of images produced from ultrasound has improved significantly. Nevertheless, further improvement is needed, particularly with respect to images involving vasculature in tissues that are perfused with a vascular blood supply. Accordingly, there is a need for improved ultrasound techniques, including improved contrast agents which are capable of providing medically useful images of the vasculature and vascular-related organs.

The reflection of sound from a liquid-gas interface is extremely efficient. Accordingly, bubbles, including gas-filled bubbles, are useful as contrast agents. Exemplary bubbles include, for example, liposomes, micelles and the like. As discussed more fully hereinafter the effectiveness of bubbles as contrast agents depends upon various factors, including, for example, the size and/or elasticity of the bubble.

With respect to the effect of bubble size, the following discussion is provided. As known to the skilled artisan, the signal which is reflected from a bubble is a function of the radius ($r^6$) of the bubble (Rayleigh Scatterer). Thus, a bubble having a diameter of 4 micrometer ($\mu$m) possesses about 64 times the scattering ability of a bubble having a diameter of 2 $\mu$m. Thus, generally speaking, the larger the bubble, the greater the reflected signal.

However, bubble size is limited by the diameter of capillaries through which the bubbles must pass. Generally, contrast agents which comprise bubbles having a diameter of greater than 10 $\mu$m can be dangerous since microvessels may be occluded. Accordingly, it is desired that greater than about 99% of the bubbles in a contrast agent have a diameter of less than 10 $\mu$m. Mean bubble diameter is important also, and should be greater than 1 $\mu$m, with greater than 2 $\mu$m being preferred. The volume weighted mean diameter of the bubbles should be about 7 to 10 micrometer.

As noted above, the elasticity of bubbles is also important. This is because highly elastic bubbles can deform, as necessary, to "squeeze" through capillaries. This decreases the likelihood of occlusion. The effectiveness of a contrast agent which comprises bubbles is also dependent on the bubble concentration. Generally, the higher the bubble concentration, the greater the reflectivity of the contrast agent.

Another important characteristic which is related to the effectiveness of bubbles as contrast agents is bubble stability. As used herein, particularly with reference to gas-filled bubbles, "bubble stability" refers to the ability of bubbles to retain gas entrapped therein after exposure to a pressure greater than atmospheric pressure. To be effective as contrast agents, bubbles generally need to retain greater than 50% of entrapped gas after exposure to pressure of 300 millimeters (mm) of mercury (Hg) for about one minute. Particularly effective bubbles retain 75% of the entrapped gas after being exposed for one minute to a pressure of 300 mm Hg, with an entrapped gas content of 90% providing especially effective contrast agents. It is also highly desirable that, after release of the pressure, the bubbles return to their original size. This is referred to generally as "bubble resilience".

Bubbles which lack desirable stability are poor contrast agents. If, for example, bubbles release the gas entrapped therein in vivo, reflectivity is diminished. Similarly, the size of bubbles which possess poor resilience will be decreased in vivo, also resulting in diminished reflectivity. Accordingly, new and/or better stabilized contrast agents and methods for providing same are needed. The present invention is directed to this, as well as other, important ends.

The present invention provides stable microbubbles created using a lipid shell which encapsulates perfluoropropane gas and in which the stabilizer mPEG-5000 is not covalently bonded to the lipid. Unexpectedly, the gas-filled microbubbles of the present invention in which the stabilizer mPEG-5000 is not covalently bonded to the lipid possess a number of surprising yet highly beneficial characteristics. The microbubble composition of the present invention provides larger microbubble diameter, improved stability and increased opacification when compared to microbubbles prepared using a lipid-mPEG-5000 conjugate. The microbubble composition of the present invention also provides economic benefits because synthesis and purification of the lipid-mPEG-5000 conjugate is not required. The gas-filled microbubbles of the present invention thus have surprisingly and unexpectedly superior characteristics for ultrasound contrast imaging.

SUMMARY OF THE INVENTION

Accordingly, one object of the present invention is to provide a composition comprising stable microbubbles in an aqueous solution.

It is another object of the present invention to provide a pharmaceutical composition comprising stable microbubbles in an aqueous solution.

It is another object of the present invention is to provide a process for manufacturing the stable microbubbles.

These and other objects, which will become apparent during the following detailed description, have been achieved by the inventors' discovery that a stable microbubbles in an aqueous solution can be conveniently and reproducibly prepared and used for ultrasound.

BRIEF DESCRIPTION OF THE DRAWINGS

The foregoing summary, as well as the following detailed description of the preferred embodiments of the present invention, will be better understood when read in conjunction with the accompanying drawings, in which:

FIG. 1 shows the calculation of attenuation values from individual attenuation spectra.

FIG. 2 is a schematic diagram of the canine two minute infusion protocol in which EOI indicates the end of infusion. FIG. 2 also shows the timing of the measurements of the fundamental and gated second harmonics.

DETAILED DESCRIPTION

Figure 1:
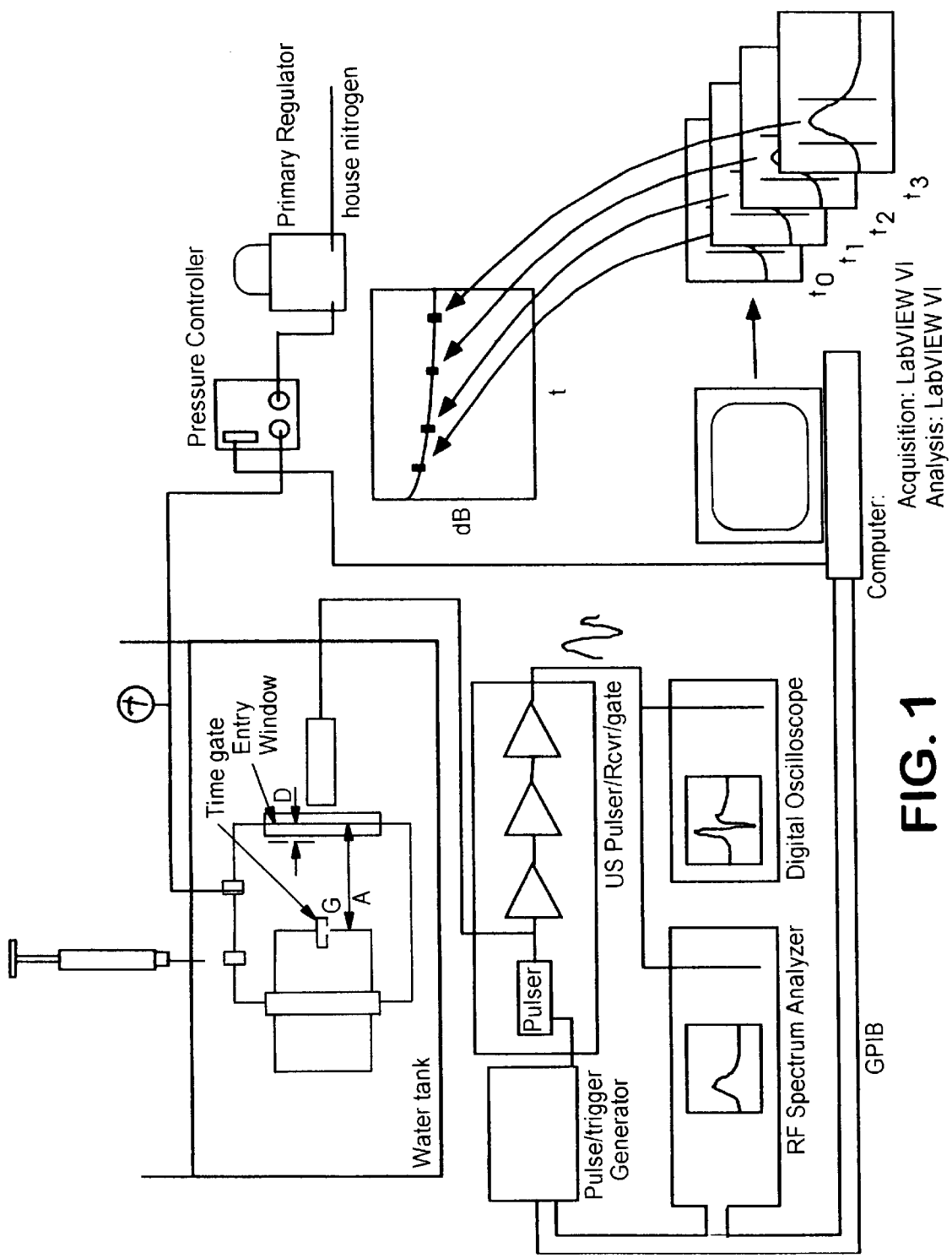
FIG. 1 is a block diagram of the acoustic attenuation system used to perform the standard pressure protocol.

In a first embodiment, the present invention provides a composition comprising, in an aqueous solution, microbubbles comprising:

(a) a lipid shell, (b) a stabilizer coated on the lipid shell and (c) perfluoropropane gas encapsulated in the lipid shell; wherein: the lipid shell comprises a blend of 1,2dipalmitoyl-sn-glycero-3-phosphatidic acid, monosodium salt, 1,2-dipalmitoyl-sn-glycero-3-phosphatidylcholine and 1,2-dipalmitoyl-sn-glycero-3-phosphatidylethanolamine, monosodium salt and the stabilizer is selected from polyethylene glycol polymers, polyethylene-polypropylene glycol and poloxamers.

In a preferred embodiment, the aqueous solution comprises water, sodium chloride and glycerine.

In another preferred embodiment, the aqueous solution of the composition further comprises: water, sodium chloride and propylene glycol.

In another preferred embodiment, the aqueous solution of the composition comprises: water, glycerine and propylene glycol.

In another preferred embodiment, the aqueous solution of the composition comprises: water, sodium chloride, glycerine and propylene glycol.

In another preferred embodiment, the aqueous solution of the composition comprises: 73–79 weight percent pharmaceutically acceptable water, 0.53–0.79 weight percent sodium chloride, 9.6–14 weight percent glycerine and 8–12 weight percent propylene glycol.

In another preferred embodiment, the aqueous solution of the composition comprises: 75–78 weight percent pharmaceutically acceptable water, 0.595–0.725 weight percent sodium chloride, 10.7–12.9 weight percent glycerine and 9–11 weight percent propylene glycol.

In another preferred embodiment, the aqueous solution of the composition comprises: 77 weight percent pharmaceutically acceptable water, 0.66 weight percent sodium chloride, 12 weight percent glycerine and 10 weight percent propylene glycol.

In another preferred embodiment, the lipid shell of the composition comprises: 0.0035–0.0054 weight percent 1,2-dipalmitoyl-sn-glycero-3-phosphatidic acid, monosodium salt, 0.035–0.043 weight percent 1,2-dipalmitoyl-sn-glycero-3-phosphatidylcholine and 0.0033–0.004 weight percent 1,2-dipalmitoyl-sn-glycero-3-phosphatidylethanolamine, monosodium salt.

In another preferred embodiment, the lipid shell of the composition comprises: 0.0038–0.0049 weight percent 1,2-dipalmitoyl-sn-glycero-3-phosphatidic acid, monosodium salt, 0.037–0.041 weight percent 1,2-dipalmitoyl-sn-glycero-3-phosphatidylcholine and 0.0035–0.0039 weight percent 1,2-dipalmitoyl-sn-glycero-3-phosphatidylethanolamine, monosodium salt.

In another preferred embodiment, the lipid shell of the composition comprises: 0.0043 weight percent 1,2-dipalmitoyl-sn-glycero-3-phosphatidic acid, monosodium salt, 0.039 weight percent 1,2-dipalmitoyl-sn-glycero-3-phosphatidylcholine and 0.0037 weight percent 1,2-dipalmitoyl-sn-glycero-3-phosphatidylethanolamine, monosodium salt.

In another preferred embodiment, the polyethylenepolypropylene glycol and poloxamer stabilizer of the composition are selected from Poloxamer 407 (Pluronic F127), Poloxamer 338 (Pluronic F108) and Poloxamer 188 (Pluronic).

In another preferred embodiment, the stabilizer of the composition comprises methoxypolyethylene glycol 5000 carbamoyl.

In another preferred embodiment, the stabilizer of the composition comprises 0.024–0.029 weight percent methoxypolyethylene glycol 5000 carbamoyl.

In another preferred embodiment, the stabilizer of the composition comprises 0.025–0.028 weight percent methoxypolyethylene glycol 5000 carbamoyl.

In another preferred embodiment, the stabilizer of the composition comprises 0.027 weight percent methoxypolyethylene glycol 5000 carbamoyl.

In another preferred embodiment, the microbubbles of the composition have diameters in the range of greater than or equal to 10 µm.

In another preferred embodiment, the microbubbles of the composition have diameters in the range of 1–10 µm.

In another preferred embodiment, the microbubbles of the composition have diameters in the range of 1–2 µm.

In another preferred embodiment, a vial contains the composition of the invention.

In a second embodiment, the present invention provides a pharmaceutical composition for diagnostic use which comprises: an aqueous solution, 1,2-dipalmitoyl-sn-glycero-3-phosphatidic acid, monosodium salt, 1,2-dipalmitoyl-sn-glycero-3-phosphatidylcholine and 1,2-dipalmitoyl-sn-glycero-3-phosphatidylethanolamine, monosodium salt, methoxypolyethylene glycol 5000 carbamoyl and perfluoropropane gas.

In a preferred embodiment, the aqueous solution of the pharmaceutical composition comprises water, sodium chloride and glycerine.

In another preferred embodiment, the aqueous solution of the pharmaceutical composition comprises water, sodium chloride and propylene glycol.

In another preferred embodiment, the aqueous solution of the pharmaceutical composition comprises water, glycerine and propylene glycol.

In another preferred embodiment, the aqueous solution of the pharmaceutical composition comprises water, sodium chloride, glycerine and propylene glycol.

In another preferred embodiment, the aqueous solution of the pharmaceutical composition comprises 73–79 weight percent pharmaceutically acceptable water, 0.53–0.79 weight percent sodium chloride, 9.6–14 weight percent glycerine and 8–12 weight percent propylene glycol.

In another preferred embodiment, the aqueous solution of the pharmaceutical composition comprises 75–78 weight percent pharmaceutically acceptable water, 0.595–0.725 weight percent sodium chloride, 10.7–12.9 weight percent glycerine and 9–11 weight percent propylene glycol.

In another preferred embodiment, the aqueous solution of the pharmaceutical composition comprises 77 weight percent pharmaceutically acceptable water, 0.66 weight percent sodium chloride, 12 weight percent glycerine and 10 weight percent propylene glycol.

In another preferred embodiment, the lipid shell of the pharmaceutical composition comprises 0.0035–0.0054 weight percent 1,2-dipalmitoyl-sn-glycero-3-phosphatidic acid, monosodium salt, 0.035–0.043 weight percent 1,2-dipalmitoyl-sn-glycero-3-phosphatidylcholine and 0.0033–0.004 weight percent 1,2-dipalmitoyl-sn-glycero-3-phosphatidylethanolamine, monosodium salt.

In another preferred embodiment, the lipid shell of the pharmaceutical composition comprises 0.0038–0.0049 weight percent 1,2-dipalmitoyl-sn-glycero-3-phosphatidic acid, monosodium salt, 0.037–0.041 weight percent 1,2-dipalmitoyl-sn-glycero-3-phosphatidylcholine and 0.0035–0.0039 weight percent 1,2-dipalmitoyl-sn-glycero-3-phosphatidylethanolamine, monosodium salt.

In another preferred embodiment, the lipid shell of the pharmaceutical composition comprises 0.0043 weight percent 1,2-dipalmitoyl-sn-glycero-3-phosphatidic acid, monosodium salt, 0.039 weight percent 1,2-dipalmitoyl-sn-glycero-3-phosphatidylcholine and 0.0037 weight percent 1,2-dipalmitoyl-sn-glycero-3-phosphatidylethanolamine, monosodium salt.

In a third embodiment, the composition of the present invention is prepared by the process comprising:
(1) contacting a lipid blend with propylene glycol at 55° C., whereby the lipid blend substantially dissolves in the propylene glycol;
(2) contacting the solution from step (1) with the aqueous solution to form a lipid suspension;
(3) adjusting the pH of the solution to 6.5;
(4) heating the lipid suspension from step (2) to 75° C.;
(5) filtering the lipid suspension through a sterilizing filter;
(6) dispensing the filtered solution from step (5) into a vial; and
(7) exchanging the headspace gas of the vial from step (6) with a perfluorocarbon gas.

In a preferred embodiment, the process for preparing the composition of the invention further comprises:
(8) agitating the vial from step (7) for 45 seconds in a shaking apparatus at approximately 3200 oscillations/minute to form the microbubbles and
(9) inverting the vial from step (8) ten times at one second/inversion.

In a fourth embodiment, the pharmaceutical composition of the invention is prepared by the process comprising:
(1) contacting a lipid blend with propylene glycol at 55° C., whereby the lipid blend substantially dissolves in the propylene glycol;
(2) contacting the solution from step (1) with the aqueous solution to form a lipid suspension;
(3) adjusting the pH of the solution to 6.5;
(4) heating the lipid suspension from step (2) to 75° C.;
(5) filtering the lipid suspension through a sterilizing filter;
(6) dispensing the filtered solution from step (5) into a vial; and
(7) exchanging the headspace gas of the vial from step (6) with a perfluorocarbon gas.

In a preferred embodiment, the the process for preparing the pharmaceutical composition of the invention further comprises:
(8) agitating the vial from step (7) for 45 seconds in a shaking apparatus at approximately 3200 oscillations per minute to form microbubbles and
(9) inverting the vial from step (8) ten times at one second per inversion.

In another preferred embodiment, a vial contains the pharmaceutical composition of the invention.

In another preferred embodiment, a vial containing the composition of the invention is prepared by the above processes.

In another preferred embodiment, a vial containing the pharmaceutical composition of the invention is prepared by the above processes.

In a fifth embodiment, the invention comprises a method for imaging an internal region of a patient comprising (a) administering to the patient the composition of the invention and (b) scanning the patient using ultrasound to obtain a visible image.

In another embodiment, the invention comprises a method for imaging an internal region of a patient comprising (a) administering to the patient the pharmaceutical composition of the invention and (b) scanning the patient using ultrasound to obtain a visible image.

In another embodiment, the invention comprises a method for diagnosing the presence of diseased tissue in a patient comprising (a) administering to the patient the composition of the invention and (b) scanning the patient using ultrasound to obtain a visible image.

In another embodiment, the invention comprises a method for diagnosing the presence of diseased tissue in a patient comprising (a) administering to the patient the pharmaceutical composition of the invention and (b) scanning the patient using ultrasound to obtain a visible image.

As employed above and throughout the disclosure, the following terms, unless otherwise indicated, shall be understood to have the following meanings.

"Vesicle" refers to a spherical entity which is characterized by the presence of an internal void. Preferred vesicles are formulated from lipids, including the lipids described herein. In any given vesicle, the lipids may be in the form of a monolayer or bilayer, and the mono- or bilayer lipids may be used to form one or more mono- or bilayers. In the case of more than one mono- or bilayer, the mono- or bilayers are generally concentric. The lipid vesicles described herein include such entities commonly referred to as liposomes, micelles, bubbles, microbubbles, microspheres and the like. Thus, the lipids may be used to form a unilamellar vesicle (comprised of more than about three monolayers of bilayers) or a multilamellar vesicle (comprised of more than about three monolayers or bilayers). The internal void of the vesicles may be filled with a liquid, including, for example, an aqueous liquid, a gas, a gaseous precursor, and/or a solid or solute material, including, for example, a bioactive agent, as desired.

The term "microbubbles", as used herein, refers to vesicles which are generally characterized by the presence of one or more membranes or walls surrounding an internal void that is filled with a gas or precursor thereto. Exemplary microbubbles include, for example, liposomes, micelles and the like. As discussed more fully hereinafter, the effectiveness of microbubbles as contrast agents depends upon various factors, including, for example, the size and/or elasticity of the microbubble.

"Stabilizing material" refers to a substance which is biocompatible and which is capable of promoting the formation of vesicles in a lipid composition. As used herein, "stabilizing material" refers also to a substance which is biocompatible and which is capable of improving the stability of a vesicle. In certain preferred embodiments, the stabilizing material comprises a polymer. "Polymer", as used herein, refers to molecules formed from the chemical union of two or more repeating units. Accordingly, included within the term "polymer" are, for example, dimers, trimers and oligomers. Preferred are high molecular weight polymers such as polyethylene glycol polymers, polyethylene-polypropylene glycol and poloxamers. Especially preferred is methoxypolyethylene glycol 5000 carbamoyl. In certain other preferred embodiments, the stabilizing material comprises a non-polymeric material, including, for example, monomeric molecules. Encompassed also in the definition of "stabilizing material" are certain of the present bioactive agents. The stabilizing material may be neutral or positively or negatively charged.

The stabilizing materials comprise neutral or positively or negatively charged materials. The neutral stabilizing materials include lipidic and/or oily materials, polyalcohol polymers, glycosaminoglycans, carbohydrates, including monosaccharides, disaccharides and polysaccharides, gums and cellulosic materials. Other neutral stabilizing materials include, for example, oils, such as peanut oil, canola oil, olive oil, safflower oil and corn oil; lecithin; sphingomyelin; cholesterol and derivatives thereof; squalene; terpenes and terpenoid compounds; triglycerides; gums, such as xanthan, tragacanth, locust bean, guar and carrageenan gums; methoxylated pectin; starch; agarose; cellulose and semi-synthetic cellulose, for example, methyl cellulose, hydroxy-ethyl cellulose, methoxy cellulose and hydroxypropyl cellulose; acacia; agar; bentonites, including purified bentonite; magma; carbomer 934 P; dextrin; gelatin; di- and trihydroxy substituted alkanes and their polymers, including polyvinylalcohol; mono-, di- and triglycerides; amino alcohols; monosaccharides or sugar alcohols, such as erythrose, threose, ribose, arabinose, xylose, lyxose, fructose, sorbitor, mannitol and sedoheptulose, with preferred monosaccharides being fructose, mannose, xylose, arabinose, mannitol and sorbitol; and disaccharides, such as lactose, sucrose, maltose and cellobiose.

Positively charged stabilizing materials include compounds containing, for example, protonated or quarternary amino groups, including polymers in which the repeating units contain one or more amino groups, such as peptides, polypeptides, proteins and lipoproteins, such as albumin and natural lipoproteins. Positively charged stabilizing materials include, for example, chitin; alkanolamines, such as monoethanolamine, diethanolamine and triethanolamine, and mixtures thereof, including, for example, trolamine; polylysine; polyarginine; polyethyleneimine; chitosan; and peptides, including melanin concentrating hormone and dynorphin. Suitable negatively charged materials are compounds containing, for example, carboxy groups, including polycarboxy polymers. Negatively charged stabilizing materials include, for example, carboxymethylcellulose; salts of alginic acid, such as sodium and calcium alginate; salts of glycosaminoglycans, including salts of hyaluronic acid; phosphorylated and sulfonated derivatives of carbohydrates; genetic material, such as interleukin-2 and interferon; phosphorothioate oligomers; and negatively charged peptides, such as deltorphin. Other stabilizing materials, in addition to those exemplified above, would be apparent to one of ordinary skill in the art based on the present disclosure.

A variety of different gases may be employed in the gaseous phase of the present invention. Suitable gases include, but are not limited to, the fluorinated gases, fluorocarbon gases, and perfluorocarbon gases which are expected to provide useful ultrasound contrast properties. Particularly preferred are the perfluorocarbon gases including perfluoropropane, perfluorobutane, perfluorocyclobutane, perfluoromethane, perfluoroethane and perfluoropentane, especially perfluoropropane. Preferably, the perfluorocarbon gases have less than six carbon atoms, e.g., $CF_4$, $C_2F_6$, $C_3F_8$, cyclo-$C_4F_8$, $C_4F_{10}$, $C_5F_{12}$, cyclo-$C_5F_{10}$, cyclo-$C_4F_7$ (1-trifluoromethyl), propane (2-trifluoromethyl)-1,1,1,3,3,3 hexafluoro, and butane (2-trifluoromethyl)-1,1,1,3,3,3,4,4,4 nonafluoro. Also preferred are the corresponding unsaturated versions of the above compounds, for example $C_2F_4$, $C_3F_6$, the isomers of $C_4F_8$. The halogenated versions of hydrocarbons, where other halogens are used to replace F (e.g., Cl, Br, I) would also be useful, but may not be as desirable as the perfluorinated versions. Also, mixtures of these gases, especially mixtures of perfluorocarbons with other perfluorocarbons and mixtures of perfluorocarbons with other inert gases, such as air, $N_2$, $O_2$, He, would be useful.

Other features of the invention will become apparent in the course of the following descriptions of exemplary embodiments which are given for illustration of the invention and are not intended to be limiting thereof.

EXAMPLES

Example 1

Preparation of Microbubbles of the Present Invention

A 200 mL batch of lipid/polymer solution was compounded for dispensing to final vials. All lipids used were removed from the approximately 20° C. storage and allowed to equilibrate to room temperature. A Neslab waterbath was set to 55° C. The three lipids and polymer, DPPA (9 mg), DPPC (82 mg), DPPE (7.6 mg), mPEG-5000 (55 mg) were weighed into a volumetric flask. To the flask, 20 mL of propylene glycol was added. The solution was placed in the waterbath set at 55° C. To the heated solution, 120 mL of WFI (water for injection) was added. In a separate compounding flask, sodium chloride (1.36 g) was added and the flask was agitated to aid in mixing. Glycerine (20 mL, 25.244 g) was then weighed into the compounding flask and the solution was again mixed by agitation. The compounding flask containing the sodium chloride/glycerine solution was placed into the waterbath at 55° C. When the lipids/polymer were dissolved into the propylene glycol, the solution was added to the sodium chloride/glycerine solution. During the transfer the flask was rinsed with 55° C. WFI. The compounding flask was brought to a final volume of 200 mL with WFI heated to 55° C. The solution was allowed to cool to room temperature and a pH measurement was made. The pH was adjusted to 6.5 using 0.1N NaOH or 0.1N HCl as needed. The compounding flask was then placed in a waterbath at 70–75° C. until solution remained at that temperature for 10 minutes.

Dispensing

The compounding solution was allowed to cool to room temperature, after which 1.63 mL was dispensed into individual vials with stoppers placed in the lyophilization position.

Headspace Adjustment/Capping

Vials were placed in the FTS freeze dryer which was then evacuated to 74 torr. A perfluoropropane (PFP) tank was attached to the freeze dryer and allowed to bleed PFP until the chamber pressure reached 735 torr. Vials were stoppered and freeze dryer shelves remained in the compressed position. The freeze dryer was then purged using nitrogen for 20 minutes to remove excess PFP. Vials were removed and crimped. All vials were stored at 4° C.

Example 2

Preparation of Microbubbles of the Prior Art using Coupled Lipid-Stabilizer

The mirobubbles in this example were prepared using the procedure of Exampe 1 and a lipid-mPEG-5000 conjugate instead of lipid that is not conjugated to mPEG-5000.

Example 3

Microbubble Particle Size Protocol

Samples were analyzed using an AccuSizer Model 770 Optical Particle Analyzer. This technique employs Single Particle Optical Sizing. Particles in a diluent are made to flow across a photozone (a narrow region of uniform illumination). The particle gives rise to a signal pulse in the optical detector, the magnitude of the pulse proportional to the particle diameter. A particle size distribution is constructed in real time, during an autodilution step, by comparing the measured pulse height with a standard calibration curve.

A standard protocol was followed for the analysis of the particle size distribution and concentration, for particles in the size range 1 to 500 $\mu$m. The vial of interest was shaken on a Vialmix shaking apparatus for 45 seconds at approximately 3200 oscillations per minute to form a solution of microbubbles. The sample vial was allowed to sit for 5 minutes, after which time the vial was manually inverted 10 times, one second per inversion to disperse the formed microbubbles in the solution. After manual dispersion, a 3 $\mu$L sample of the shaken solution was removed with a Hamilton syringe and carefully injected into the AccuSizer sample reservoir containing 60 mL of MilliQ water. The sample was then analyzed by the sizer using an autodilution process, with the diluent being MilliQ water. When the data acquisition was completed, a histogram of the resulting particle size distribution was presented with the corresponding particle concentration. Prior to additional analysis, the sample reservoir was thoroughly cleaned and background particle counts monitored until appropriate background levels were obtained.

The results of the particle size tests indicate that the microbubble composition of Example 1, which contains lipid that is not conjugated to the stabilizer, exhibits a particle size distribution containing a large ratio of particles in the 1–5 $\mu$m diameter. It has been demonstrated that microbubbles with diameters of a 1–5 $\mu$m exhibit increased opacification properties and are therefore more effective ultrasound contrast agents than smaller microbubbles.

Example 4

Standard Pressure Test Protocol

Measurement of attenuation for contrast agents is the simplest and most reliable single method for assessing acoustic activity. It uses an ultrasound-derived signal with a high signal-to-noise ratio and it has a very wide dynamic range, excellent reproducibility and is linearly related to the concentration of the bubbles. The measurement is a straightforward implementation of the attenuation portion of the method of Madsen, et al., J. Acoust. Soc. Am. 76(3): 913–923 (1984). The behavior of the attenuation over time and with differing ambient pressure yields a measure of the bubbles' response to some of the stresses similar to those observed clinically.

The basic ultrasound in-vitro test system permits a number of assays to be performed. In all tests, material to be assayed was introduced into a closed, temperature-controlled test cell filled with a fresh preparation of air-saturated physiological saline at 37° C. Sample introduction was accomplished either by direct injection of 25 $\mu$L of composition of Example 1 from the vial, or introduction of 10 cc of saline into which the 25 $\mu$L sample of the composition of Example 1 had been prediluted. Final dilution of the test material was 1 part in 20,000 (except for dilution-related operational verification studies). FIG. 1 is a schematized diagram of the system showing components and data flow. Control, acquisition and analysis software was written using LabView (National Instruments, Austin, Tex.) for the Macintosh.

Testing is done by observing the change in the intensity of ultrasound from a focused, 2.25 MHz broadband transducer driven at a low level with a single cycle pulse. All signals were derived from energy reflected back from a stainless steel cylinder protruding into the test cell. Data was acquired by routing the radiofrequency signal returned from the transducer through amplification and time gating (set to correspond to the signal from the reflector only) to a spectrum analyzer and then to a computer. A reference spectrum (in dB) was acquired just prior to introduction of the agent and subsequent spectra were acquired at one-minute intervals for ten minutes following agent introduction. These were stored on disk.

During analysis, the spectrum for the acquisition at each time point was subtracted from the preinjection spectrum.

The difference spectra were then linearized and averages determined by using a 70% bandwidth centered at 2.25 MHz. The average was then reconverted to decibels. For purposes of intercomparison of materials, two parameters were reported: the attenuation at the second time point and the decay constant resulting from a nonlinear regression of a single-term exponential. For each material to be tested, at least two samples from at least two vials of a given lot were examined.

The cell is capable of pressurization to a maximum of 225 mmHg and the acoustic attenuation may be measured before, during and after pressurization as required. In general, the software permits any sequence of pressure variations with a maximum of eighteen measurements (and eighteen pressure values) and varying time intervals between measurements. Pressure calibration was performed using a NIST-traceable pressure calibrator (Meri-Cal model LP200I, Meriam Instrument Co., Cleveland, Ohio). The software required that calibration be performed at least once on every day when data was taken.

In this mode, two sequences have been used. In the first (subsequently referred to as the "standard pressurization protocol"), six measurements in addition to the reference measurement were taken at one minute intervals. The first two were at atmospheric pressure, the second two at 88 mmHg and the third pair at 135 mmHg. The second sequence, (subsequently referred to as the "fine-step pressurization protocol") uses 18 measurements taken approximately every 20 seconds, in which the pressure was increased from 0 mmHg gauge in steps of 10 mmHg at each measurement to a maximum pressure of 100 mmHg.

The results of the pressure test suggest that the microbubble composition of Example 1, which contains lipid that is not conjugated to the stabilizer, exhibits improved stability when compared to the microbubble composition of Example 2 which contains lipid conjugated to the stabilizer.

Utility

The pharmaceuticals of the present invention are useful for ultrasound diagnosis. The pharmaceutical compositions of the present invention which relate to a microbubble composition comprised of a lipid shell, a stabilizer coated on the lipid shell and perfluoropropane gas encapsulated in the lipid shell are useful in ultrasound imaging for studying various areas of the body including the vasculature and tissue microvasculature.

Representative compounds of the present invention were tested in the following in vivo model and were found to be active.

Canine In Vivo Assay

Gas-filled liposomes have been proposed as a contrast enhancing medium for clinical ultrasound which will aid in the diagnosis of left ventricular wall motion defects, left ventricular wall motion, myocardial perfusion and monitoring flow through various capillary beds. The composition of Example 1 is a PFP filled liposome which was designed for intravenous administration and elicits an enhancement of the heart as visualized by ultrasound. This procedure has been found to be significantly simpler to perform relative to angiography since these studies can be performed at the patient's bedside or in an outpatient setting.

The microbubble compositions of Examples 1 and 2 were assessed in the canine two minute infusion protocol with doses of 30, 100 and 300 µl/kg. In this protocol both fundamental left ventricular and gated second harmonic myocardial imaging is performed using a prototype Sonos 2500 (Hewlett Packard).

General Methods

Adult beagle dogs of either sex (9–13 kg) were anesthetized with pentobarbital sodium (35 mg/kg,i.v.) and ventilated with room air via an endotracheal tube (12 strokes/min, 25 ml/kg). For arterial pressure determination, the right femoral artery was cannulated with a saline-filled polyethylene catheter (PE 240) and connected to a Statham pressure transducer (P23 ID; Oxnard, Calif.). Mean arterial blood pressure was determined via damping the pulsatile pressure signal. Heart rate and ECG were monitored using a cardiotachometer (Biotech, Grass Quincy, Mass.) triggered from a lead II electrocardiogram generated by limb leads. The right femoral vein was cannulated (PE240) for drug administrations. A 5F pressure tip catheter (SPC-350; Millar, Tex.) was advanced down the left carotid artery into the left ventricle. Placement was determined via the pulsatile pressure waveform via a transducer control unit (TC-510; Millar, Tex.) and measurement of the first derivative of left ventricular pressure (dP/dt) was determined. After placement of all hemodynamic catheters, a left thoracotomy was performed. The heart was suspended in a pericardial cradle and a gel standoff pad was placed on top of the heart to serve as an interface between the heart and probe. All parameters, including eft ventricular pressure, end-diastolic pressure, dP/dt, EKG, heart rate, and arterial pressure, were monitored continuously on a polygraph recorder (model 7 E Grass) at a paper speed of 10 mm/min or 25 mm/sec. Platelet, RBC counts, hemoglobin and hematocrit determinations were performed on whole blood collected in 2 mg/ml disodium EDTA using a Sysmex™ K1000 (Baxter laboratories, McGraw Park, Ill.). Particle sizing of each vial of microbubbles was determined post each infusion via an Accusizer with an auto dilutor (Model 770; Particle Sizing Systems, Ca.).

Protocol

Using a 1.8/3.6 MHz echocardiographic probe placed on the left side of the heart, short axis papillary muscle views were recorded. Ultrasonic settings were held constant throughout the duration of the study as shown in FIG. 2. After a period of stabilization, baseline hematology, hemodynamics and ultrasonic images, including fundamental left ventricular opacification and gated second harmonic images every tenth systolic beat, were obtained prior to each infusion dose.

Each lot of microbubbles was prepared using a Vialmix™ set for 45 seconds of agitation. After shaking, each vial was allowed to stand at room temperature for 5 minutes. The vial was then inverted manually ten times prior to withdrawing an infusion sample. Infusion samples were withdrawn using an 18G needle and 1 cc syringe and diluted in a saline tube at a concentration of 30, 100 and 300 µl/kg/2 ml. Each preparation of microbubbles was inverted manually again ten times prior to infusion. Infusion of each preparation occurred through the right femoral vein over two minutes.

Fundamental left ventricular opacification imaging was performed 10 seconds after the start of each dose using 1.8 MHz. Images were recorded for a period of ten seconds at which time, analysis was switched from fundamental to gated second harmonic (1.8/3.6 MHz) imaging every tenth systolic cardiac cycle. Images were recorded using this method 30 seconds from the start of infusion for 20 seconds. The imaging cycle was then repeated every minute from the start of infusion for each dose until visualization of material dissipated. Hemodynamic and hematological values were obtained post-infusion and just prior to the administration of the next dose.

Image Analysis

Images were transferred off line to NIH Image for analysis of video intensities. Three 15×15 boxes were placed in different areas within the region of interest and intensities were averaged. The video intensities were then plotted against time to generate time/intensity curves for left ventricular opacification (LVO), left circumflex coronary artery (LCX), left anterior coronary artery (LAD) and right coronary artery (RCA) perfusion.

The results of the in vivo imaging studies in the dog model demonstrated the superior properties of the microbubble composition of Example 1 when compared with the microbubble composition of Example 2. The microbubble composition of Example 1 which contains lipid that is not conjugated to the stabilizer, provided perfusion with similar intensity and duration of the microbubble composition of Example 2. However, significantly less particles per injected dose were required to achieve those results when the studies were performed using the microbubble composition of the invention. Furthermore, the same dose of the microbubble composition of the present invention provided enhanced and prolonged left ventricular opacification when compared with the microbubble composition containing the lipid-mPEG-5000 conjugate.

In conclusion, the comparative in vitro and in vivo studies demonstrate that the microbubble composition containing lipid that is not conjugated to the stabilizer provides superior ultrasound contrast agent properties, including larger microbubble diameter, improved stability and increased opacification.

Obviously, numerous modifications and variations of the present invention are possible in light of the above teachings. It is therefore to be understood that within the scope of the appended claims, the invention may be practiced otherwise that as specifically described herein.

What is claimed is:

1. A composition comprising, in an aqueous solution, microbubbles comprising:
   (a) a lipid shell,
   (b) a stabilizer coated on the lipid shell and
   (c) perfluoropropane gas encapsulated in the lipid shell;
   wherein: the lipid shell comprises a blend of 1,2-dipalmitoyl-sn-glycero-3-phosphatidic acid, monosodium salt, 1,2-dipalmitoyl-sn-glycero-3-phosphatidylcholine and 1,2-dipalmitoyl-sn-glycero-3-phosphatidylethanolamine, monosodium salt and wherein the stabilizer comprises methoxypolyethylene glycol 5000 carbamoyl that is not conjugated to the lipid shell.

2. A composition of claim 1 wherein the aqueous solution comprises water, sodium chloride and glycerine.

3. A composition of claim 1 wherein the aqueous solution comprises water, sodium chloride and propylene glycol.

4. A composition of claim 1 wherein the aqueous solution comprises water, glycerine and propylene glycol.

5. A composition of claim 1 wherein the aqueous solution comprises water, sodium chloride, glycerine and propylene glycol.

6. A composition of claim 1 wherein the aqueous solution comprises 73–79 weight percent pharmaceutically acceptable water, 0.53–0.79 weight percent sodium chloride, 9.6–14 weight percent glycerine and 8–12 weight percent propylene glycol.

7. A composition of claim 6 wherein the aqueous solution comprises 75–78 weight percent pharmaceutically acceptable water, 0.595–0.725 weight percent sodium chloride, 10.7–12.9 weight percent glycerine and 9–11 weight percent propylene glycol.

8. A composition of claim 7 wherein the aqueous solution comprises 77 weight percent pharmaceutically acceptable water, 0.66 weight percent sodium chloride, 12 weight percent glycerine and 10 weight percent propylene glycol.

9. A composition of claim 1 wherein the lipid shell comprises 0.0035–0.0054 weight percent 1,2-dipalmitoyl-sn-glycero-3-phosphatidic acid, monosodium salt, 0.035–0.043 weight percent 1,2-dipalmitoyl-sn-glycero-3-phosphatidylcholine and 0.0033–0.004 weight percent 1,2-dipalmitoyl-sn-glycero-3-phosphatidylethanolamine, monosodium salt.

10. A composition of claim 9 wherein the lipid shell comprises 0.0038–0.0049 weight percent 1,2-dipalmitoyl-sn-glycero-3-phosphatidic acid, monosodium salt, 0.037–0.041 weight percent 1,2-dipalmitoyl-sn-glycero-3-phosphatidylcholine and 0.0035–0.0039 weight percent 1,2-dipalmitoyl-sn-glycero-3-phosphatidylethanolamine, monosodium salt.

11. A composition of claim 10 wherein the lipid shell comprises 0.0043 weight percent 1,2-dipalmitoyl-sn-glycero-3-phosphatidic acid, monosodium salt, 0.039 weight percent 1,2-dipalmitoyl-sn-glycero-3-phosphatidylcholine and 0.0037 weight percent 1,2-dipalmitoyl-sn-glycero-3-phosphatidylethanolamine, monosodium salt.

12. A composition of claim 1 wherein the stabilizer comprises 0.024–0.029 weight percent methoxypolyethylene glycol 5000 carbamoyl.

13. A composition of claim 12 wherein the stabilizer comprises 0.025–0.028 weight percent methoxypolyethylene glycol 5000 carbamoyl.

14. A composition of claim 13 wherein the stabilizer comprises 0.027 weight percent methoxypolyethylene glycol 5000 carbamoyl.

15. A composition of claim 1 wherein the microbubbles have diameters in the range of greater than or equal to 10 $\mu$m.

16. A composition of claim 1 wherein the microbubbles have diameters in the range of 1–10 $\mu$m.

17. A composition of claim 16 wherein the microbubbles have diameters in the range of 1–2 $\mu$m.

18. A vial containing the composition of claim 1.

19. A pharmaceutical composition for diagnostic use comprising an aqueous solution, 1,2-dipalmitoyl-sn-glycero-3-phosphatidic acid, monosodium salt, 1,2-dipalmitoyl-sn-glycero-3-phand 1,2-dipalmitoyl-sn-glycero-3-phosphatidylethanolamine, monosodium salt, methoxypolyethylene glycol 5000 carbamoyl and perfluoropropane gas;
   wherein the methoxypolyethylene glycol 5000 carbamoyl is not conjugated to a lipid.

20. A pharmaceutical composition of claim 19 wherein the aqueous solution comprises water, sodium chloride and glycerine.

21. A pharmaceutical composition of claim 19 wherein the aqueous solution comprises water, sodium chloride and propylene glycol.

22. A pharmaceutical composition of claim 19 wherein the aqueous solution comprises water, glycerine and propylene glycol.

23. A pharmaceutical composition of claim 19 wherein the aqueous solution comprises water, sodium chloride, glycerine and propylene glycol.

24. A pharmaceutical composition of claim 19 wherein the aqueous solution comprises 73–79 weight percent pharmaceutically acceptable water, 0.53–0.79 weight percent sodium chloride, 9.6–14 weight percent glycerine and 8–12 weight percent propylene glycol.

25. A pharmaceutical composition of claim 24 wherein the aqueous solution comprises 75–78 weightlpercent pharmaceutically acceptable water, 0.595–0.725 weight percent sodium chloride, 10.7–12.9 weight percent glycerine and 9–11 weight percent propylene glycol.

26. A pharmaceutical composition of claim 25 wherein the aqueous solution comprises 77 weight percent pharmaceutically acceptable water, 0.66 weight percent sodium chloride, 12 weight percent glycerine and 10 weight percent propylene glycol.

27. A pharmaceutical composition of claim 19 wherein the lipid shell comprises 0.0035–0.0054 weight percent 1,2-dipalmitoyl-sn-glycero-3-phosphatidic acid, monosodium salt, 0.035–0.043 weight percent 1,2-dipalmitoyl-sn-glycero-3-phosphatidylcholine and 0.0033–0.004 weight percent 1,2-dipalmitoyl-sn-glycero-3-phosphatidylethanolamine, monosodium salt.

28. A pharmaceutical composition of claim 27 wherein the lipid shell comprises 0.0038–0.0049 weight percent 1,2-dipalmitoyl-sn-glycero-3-phosphatidic acid, monosodium salt, 0.037–0.041 weight percent 1,2-dipalmitoyl-sn-glycero-3 phosphatidylcholine and 0.0035–0.0039 weight percent 1,2-dipalmitoyl-sn-glycero-3-phosphatidylethanolamine, monosodium salt.

29. A pharmaceutical composition of claim 28 wherein the lipid shell comprises 0.0043 weight percent 1,2-dipalmitoyl-sn-glycero-3-phosphatidic acid, monosodium salt, 0.039 weight percent 1,2-dipalmitoyl-sn-glycero-3-phosphatidylcholine and 0.0037 weight percent 1,2-dipalmitoyl-sn-glycero-3-phosphatidylethanolamine, monosodium salt.

30. A composition comprising, in an aqueous solution, microbubbles comprising:
    (a) a lipid shell; (b) a stabilizer coated on the lipid shell; and (c) perfluoropropane gas encapsulated in the lipid shell, wherein the lipid shell comprises a blend of 1,2-dipalmitoyl-sn-glycero-3-phosphatidic acid, monosodium salt, 1,2-dipalmitoyl-sn-glycero-3-phosphatidylcholine and 1,2-dipalmitoyl-sn-glycero-3-phosphatidylethanolamine, monosodium salt and wherein the stabilizer comprises methoxypolyethylene glycol 5000 carbamoyl that is not conjugated to the lipid shell, said composition prepared by the process comprising the steps of:
    (1) contacting a mixture of the lipid blend and the stabilizer with propylene glycol at 55° C., whereby the mixture substantially dissolves in the propylene glycol to form absolution;
    (2) contacting the solution from step (1) with an aqueous solution to form a lipid solution;
    (3) adjusting the pH of the lipid solution to 6.5;
    (4) heating the lipid solution from step (3) to 75° C.;
    (5) filtering the lipid solution through a sterilizing filter;
    (6) dispensing the filtered solution from step (5) into a vial; and
    (7) exchanging the headspace gas of the vial from step (6) with a perfluorocarbon gas.

31. A composition prepared by the process according to claim 30, ewherein the process further comprises:
    (8) agitating the vial from step (7) for 45 seconds in a shaking apparatus at approximately 3200 oscillations/minute to form the microbubbles and
    (9) inverting the vial from step (8) ten times at one second/inversion.

32. A pharmaceutical composition for diagnostic use comprising an aqueous solution, 1,2-dipalmitoyl-sn-glycero-3-phosphatidic acid, monosodium salt, 1,2-dipalmitoyl-sn-glycero-3-phosphatidylcholine and 1,2-dipalmitoyl-sn-glycero-3-phosphatidylethanolamine, monosodium salt, methoxypolyethylene glycol 5000 carbamoyl and perfluoropropane gas, said composition prepared by the process comprising:
    (1) contacting a mixture of a lipid blend of said 1,2-dipalmitoyl-sn-glycero-3-phosphatidic acid, monosodium salt, 1,2-dipalmitoyl-sn-glycero-3-phosphatidylcholine and 1,2 dipalmitoyl-sn-glycero-3-phosphatidylcholine and 1,2-dipa;lmitoyl -sn-glycero-3-phosphatidylethanolamine, monosodium salt and said methoxypolyethylene glycol 5000 carbamoyl with propylene glycol at 55° C., whereby the mixture substantially dissolves in the propylene glycol;
    (2) contacting the solution from step (1) with the aqueous solution to form a lipid solution;
    (3) adjusting the pH of the lipid solution to 6.5;
    (4) heating the lipid solution from step (3) to 75° C.;
    (5) filtering the lipid solution through a sterilizing filter;
    (6) dispensing the filtered solution from step (5) into a vial; and
    (7) exchanging the headspace gas of the vial from step (6) with a perfluorocarbon gas.

33. A pharmaceutical composition prepared by the process according to claim 32, wherein the process further comprises:
    (8) agitating the vial from step (7) for 45 seconds in a shaking apparatus at approximately 3200 oscillations per minute to form microbubbles and
    (9) inverting the vial from step (8) ten times at one second per inversion.

34. A vial containing the pharmaceutical composition of claim 19.

35. A vial containing the composition of claim 30.

36. A vial containing the composition of claim 31.

37. A vial containing the composition of claim 32.

38. A vial containing the composition of claim 33.

39. A method for imaging an internal region of a patient comprising (a) administering to the patient the composition of claim 1 and (b) scanning the patient using ultrasound to obtain a visible image.

40. A method for imaging an internal region of a patient comprising (a) administering to the patient the pharmaceutical composition of claim 19 and (b) scanning the patient using ultrasound to obtain a visible image.

41. A method for diagnosing the presence of diseased tissue in a patient comprising (a) administering to the patient the composition of claim 1 and (b) scanning the patient using ultrasound to obtain a visible image.

42. A method for diagnosing the presence of diseased tissue in a patient comprising (a) administering to the patient the pharmaceutical composition of claim 19 (b) scanning the patient using ultrasound to obtain a visible image.

* * * * *